United States Patent
Crandall et al.

(10) Patent No.: US 8,864,801 B2
(45) Date of Patent: Oct. 21, 2014

(54) METHOD OF DEFORMITY CORRECTION IN A SPINE USING INJECTABLE MATERIALS

(75) Inventors: Dennis G. Crandall, Mesa, AZ (US); T. Andrew Simonton, Memphis, TN (US); Sean M. Haddock, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1106 days.

(21) Appl. No.: 11/796,757

(22) Filed: Apr. 30, 2007

(65) Prior Publication Data

US 2008/0269717 A1    Oct. 30, 2008

(51) Int. Cl.
A61B 17/88    (2006.01)
A61F 2/44    (2006.01)
A61F 2/30    (2006.01)

(52) U.S. Cl.
CPC ........... *A61F 2/442* (2013.01); *A61F 2002/444* (2013.01); *A61F 2210/0061* (2013.01); *A61F 2002/30075* (2013.01); *A61F 2210/0085* (2013.01); *A61F 2002/30583* (2013.01)
USPC .......................................... 606/279; 606/105

(58) Field of Classification Search
USPC ............... 606/94, 279, 105; 623/17.11–17.16
See application file for complete search history.

(56) References Cited

U.S. PATENT DOCUMENTS

| | | | |
|---|---|---|---|
| 3,875,595 A | 4/1975 | Froning | |
| 4,676,782 A * | 6/1987 | Yamamoto et al. | 604/175 |
| 5,645,597 A | 7/1997 | Krapiva | |
| 5,702,454 A | 12/1997 | Baumgartner | |
| 6,183,518 B1 | 2/2001 | Ross et al. | |
| 6,206,921 B1 | 3/2001 | Guagliano et al. | |
| 6,264,659 B1 | 7/2001 | Ross et al. | |
| 6,346,123 B1 | 2/2002 | McKay | |
| 6,428,576 B1 * | 8/2002 | Haldimann | 623/17.16 |
| 6,436,143 B1 | 8/2002 | Ross et al. | |
| 6,595,998 B2 | 7/2003 | Johnson et al. | |
| 6,733,534 B2 | 5/2004 | Sherman | |
| 6,893,466 B2 | 5/2005 | Trieu | |
| 6,899,716 B2 | 5/2005 | Cragg | |
| 6,932,843 B2 | 8/2005 | Smith et al. | |
| 7,004,945 B2 | 2/2006 | Boyd et al. | |
| 7,008,422 B2 | 3/2006 | Foley et al. | |
| 7,014,633 B2 | 3/2006 | Cragg | |

(Continued)

OTHER PUBLICATIONS

Disc Dynamics; The DASCOR Product; http//www.discdyn.com/whatisDASCOR.html; Feb. 7, 2007.

(Continued)

*Primary Examiner* — David Bates
*Assistant Examiner* — Samuel Hanna
(74) *Attorney, Agent, or Firm* — Martin & Ferraro, LLP (57) ABSTRACT

A method is disclosed for increasing the stiffness of an intervertebral disc between vertebral bodies. The method includes providing a syringe with a needle approximately in the range of 16 to 25 gauge; providing a material having a first stage with a first viscosity adapted to flow through the needle, the material having a second stage with a second viscosity greater than the first viscosity, the second stage material having a stiffness in a range of 1.0-5.0 MPa; testing the annulus fibrosus of the disc to ensure that the annulus fibrosus has sufficient continuity so as to retain the first flowable stage material when subsequently injected into the disc; inserting the needle into the annulus fibrosus; injecting the first stage material into the disc; and permitting the first stage material to become the second stage material so as to form a load bearing implant in the disc.

36 Claims, 7 Drawing Sheets

(56) References Cited

U.S. PATENT DOCUMENTS

| | | | |
|---|---|---|---|
| 2004/0010251 A1* | 1/2004 | Pitaru et al. | 606/53 |
| 2004/0054414 A1* | 3/2004 | Trieu et al. | 623/17.16 |
| 2004/0210297 A1 | 10/2004 | Lin et al. | |
| 2004/0228901 A1* | 11/2004 | Trieu et al. | 424/426 |
| 2004/0253219 A1 | 12/2004 | Hedman | |
| 2005/0070908 A1 | 3/2005 | Cragg | |
| 2005/0102030 A1 | 5/2005 | Yuksel et al. | |
| 2005/0163819 A1 | 7/2005 | Yuksel et al. | |
| 2005/0175665 A1 | 8/2005 | Hunter et al. | |
| 2005/0245938 A1 | 11/2005 | Kochan | |
| 2006/0004458 A1 | 1/2006 | Collins et al. | |
| 2006/0009779 A1 | 1/2006 | Collins et al. | |
| 2006/0009851 A1* | 1/2006 | Collins et al. | 623/17.16 |
| 2006/0079905 A1 | 4/2006 | Beyar et al. | |
| 2006/0106392 A1 | 5/2006 | Embry | |
| 2006/0178743 A1 | 8/2006 | Carter | |
| 2006/0178747 A1 | 8/2006 | de Vries et al. | |
| 2006/0200245 A1 | 9/2006 | Trieu | |
| 2006/0206209 A1 | 9/2006 | Cragg et al. | |
| 2006/0287731 A1 | 12/2006 | Cauthen, III et al. | |
| 2007/0003525 A1 | 1/2007 | Moehlenbruck et al. | |
| 2007/0010717 A1 | 1/2007 | Cragg | |
| 2007/0233064 A1* | 10/2007 | Holt | 606/61 |

OTHER PUBLICATIONS

Singhal et al.; Early clinical results of an in situ polymerizing protein hydrogel nuclear repair system; NHS Grampian; University of Aberdeen.

Spinewave; NuCore Injectable Nucleus; http://www.spinewave.com/products/nucore.html; Feb. 7, 2007.

Troccoli, Carmelo; Spinal Surgery—New Technologies; Sector: Medical Devices & Procedures; Jul. 29, 2004; Sector Report; vFinance Investments, Inc.

* cited by examiner

METHOD OF DEFORMITY CORRECTION IN A SPINE USING INJECTABLE MATERIALS

BACKGROUND OF THE INVENTION

1. Field of the Invention

The present invention relates generally to intervertebral disc reconstruction or repair methods. More specifically, the present disclosure relates to a method for increasing the stiffness of an intervertebral disc between adjacent vertebral bodies of a spine.

2. Background of the Invention

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

The intervertebral disc functions to stabilize the spine and to distribute forces between vertebral bodies. The intervertebral disc is composed of three structures: the nucleus pulposus, the annulus fibrosis, and two vertebral end plates. These components work to absorb the shock, stress, and motion imparted to the human vertebrae. The nucleus pulposus is an amorphous hydrogel with the capacity to bind water. The nucleus pulposus is maintained within the center of an intervertebral disc by the annulus fibrosis, which is composed of highly structured collagen fibers. The vertebral end plates, composed of hyalin cartilage, separate the disc from adjacent vertebral bodies and act as a transition zone between the hard vertebral bodies and the soft disc.

Intervertebral discs may be displaced or damaged due to trauma or disease. Disruption of the annulus fibrosis may allow the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness, and paralysis. Intervertebral discs may also deteriorate due to the normal aging process. As a disc dehydrates and hardens, the disc space height will be reduced, leading to instability of the spine, decreased mobility and pain.

One way to relieve the symptoms of these conditions is by surgical removal of a portion or the entire intervertebral disc. The removal of the damaged or unhealthy disc may allow the disc space to collapse, which would lead to instability of the spine, abnormal joint mechanics, nerve damage, as well as severe pain. Therefore, after removal of the disc, adjacent vertebrae are typically fused to preserve the disc space. Spinal fusion involves inflexibly connecting adjacent vertebrae through the use of bone grafts or metals rods. Because the fused adjacent vertebrae are prevented from moving relative to one another, the vertebrae no longer rub against each other in the area of the damaged intervertebral disc and the likelihood of continued irritation is reduced. Spinal fusion, however, is disadvantageous because it restricts the patient's mobility by reducing the spine's flexibility, and it is a relatively invasive procedure.

Attempts to overcome these problems have led researchers to investigate the efficacy of implanting an artificial intervertebral disc to replace, completely or partially, the patient's damaged intervertebral disc. Disc replacement surgery generally involves removing the disc or damaged portion thereof and placement of an artificial disc in the evacuated disc space. Some desirable attributes of a hypothetical implantable disc include axial compressibility for shock absorbance, excellent durability to avoid future replacement, minimally invasive placement of the artificial disc to reduce post-operative discomfort, and biocompatibility. Existing artificial intervertebral discs include, for example, mechanically based (e.g. comprising rotational surfaces or springs), polymer based, and biopolymer based artificial discs.

Among the polymer based artificial intervertebral discs are several devices that utilize a flowable polymer. One example of such a device is U.S. Pat. No. 3,875,595, incorporated herein by reference in its entirety, which discloses an intervertebral disc prosthesis comprising a flexible bladder-like member that is inserted into the evacuated disc space. The prosthesis is anchored to the two adjacent vertebrae through the use of studs inserted into the bone and filled with a fluid, plastic, or hydrogel until the bladder expands to fill the evacuated disc space.

In another example, U.S. Pat. No. 6,264,659, incorporated herein by reference in its entirety, the nucleus pulposus is removed. A thermoplastic material is heated until its viscosity is sufficiently reduced to allow it to be injected under pressure into the annulus fibrosis. The thermoplastic then cools to body temperature and stiffens but retains sufficient resiliency to provide cushioning of the vertebrae and joint movement.

U.S. Pat. No. 6,187,048, incorporated herein by reference in its entirety, discloses an intervertebral disc implant wherein the nucleus pulposus is removed and a flowable polymer is injected into the evacuated annulus fibrosis. The flowable polymer is caused to cure in situ, forming a shaped, resiliently deformable prosthesis.

U.S. Pat. No. 6,140,452, incorporated herein by reference in its entirety, discloses an intervertebral disc implant wherein a multi-part polyurethane biocompatible polymer is injected into the evacuated disc space, preferably through the use of a cannula and arthroscope. The flowable composition then is cured in place.

Related art load bearing intervertebral disc implants, both prefabricated type implants and injectable implants formed in situ, are inserted into patients after a complete or partial removal of disc material. When disc material is removed, a healthy part of the disc is often taken, eradicating the function of the joint.

Preformed disc implants may tear or otherwise be damaged during implantation. Further, once implanted, many disc implants such as those formed of hydrogel may be expelled from the disc space through an annular defect, or other annular opening.

In-situ cured polymers inserted into the disc under pressure can leak the material into sensitive adjacent areas. Others have attempted to remedy the leakage potential after accessing the nucleus pulposus through the annulus and removing a portion of the nucleus pulposus by creating a seal to prevent the material from leaking through the created opening, an example of which is US 2006/0004458, incorporated herein by reference in its entirety.

Treatment to the disc in a most non-invasive procedure is preferred. This method allows the maximum amount of healthy tissue to remain intact, and for maximum retention of the normal neurological function.

A need exists for a method that increases the stiffness of an intervertebral disc that has sufficient continuity so as to retain a flowable material subsequently injected into the disc, and retains the material while it becomes a load bearing implant, and which preferably does so without removing disc material, and which preferably allows the disc to retain normal joint function and motion.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

In accordance with the purposes of the present invention, as embodied and broadly described herein, a method of this invention is provided for increasing the stiffness of an intervertebral disc between adjacent vertebral bodies of a spine. The intervertebral disc has an outer region being an annulus fibrosus and a central region being a nucleus pulposus. The method includes providing a syringe with a needle having a distal end approximately in the range of 16 to 25 gauge.

The method further includes providing a material having a first stage with a first viscosity adapted to flow through the needle. The material has a second stage with a second viscosity greater than the first viscosity. The second stage material has a stiffness in a range of 1.0-5.0 MPa.

The method further includes testing the annulus fibrosus of the disc to ensure that the annulus fibrosus has sufficient continuity so as to retain the first flowable stage material when subsequently injected into the disc; inserting the distal end of the needle into the annulus fibrosus; injecting the first stage material through the needle and into the disc; and permitting the first stage material to become the second stage material so as to form a load bearing implant in the disc to increase the stiffness of at least a portion of the disc.

In another embodiment, the method may include providing a syringe having a needle having a distal end approximately in a range of 18 to 23 gauge, or more preferably in a range of 19 to 22 gauge.

The provided material is preferably a polymer and more preferably a hydrogel. The permitting of the first stage material to become the second stage material may include curing the material, which may be a polymer or a hydrogel. The provided material in one embodiment has a second stage material stiffness in a range of 2.0-5.0 MPa, and in another embodiment has a second stage material stiffness in a range of 3.0-5.0 MPa. The provided material in one preferred embodiment includes a water absorption capability in a range of 10-90 percent, and more preferably in a range of 20-80 percent, and yet more preferably in a range of 20-55 percent, 20-40 percent, or 35-55 percent.

The testing of the annulus fibrosus may include injecting a dye into the disc to check for fissures, and more preferably injecting a radiolucent contrast solution.

The inserting of the distal end of the needle may include inserting the distal end of the needle through the annulus fibrosus and into the nucleus pulposus of the disc. The injecting of the first stage material through the needle and into the disc in a preferred embodiment includes injecting a polymer into the nucleus pulposus of the disc, and in an alternative embodiment includes injecting a hydrogel into the nucleus pulposus of the disc.

The permitting of the first stage material to become the second stage material includes curing the material. The permitting of the first stage material to become the second stage material so as to form a load bearing implant in the disc may improve the alignment of the vertebral bodies of the spine adjacent the disc. The permitting of the first stage material to become the second stage material so as to form a load bearing implant in the disc may in one preferred embodiment also accomplish one or more of the following: increase the lordosis of the vertebral bodies of the spine adjacent the disc, stiffen motion between the vertebral bodies of the spine adjacent the disc, and indirectly decompress nerve compression in the neuroforamina of the spine proximate the disc.

The method may include one or more of increasing the disc height with the load bearing implant; removing the distal end of the needle from the disc; and leaving a puncture from removal of the needle in the disc, the puncture being sufficiently small enough that none of the material seeps from the disc. The method may alternatively include leaving a puncture from removal of the needle in the disc, the puncture being sufficiently small enough that an insignificant amount of the material seeps from the disc, or in a further alternative, the puncture being sufficiently small enough that none the second stage material seeps from the disc.

The method in one embodiment includes not removing any of the disc before injecting the first stage material through the needle and into the disc. In particular, the method may include not removing any of the annulus fibrosus before injecting the first stage material through the needle and into the disc, or additionally or alternatively not removing any of the nucleus pulposus before injecting the first stage material through the needle and into the disc. The method in yet another embodiment includes positioning the patient to reduce loading in the area near the vertebra immediately surrounding the disc and to reduce pressure on the disc.

It is an object of the present invention to provide a method for increasing the stiffness of an intervertebral disc between adjacent vertebral bodies of a spine.

These and other objects of the present invention will be apparent from review of the following specification and the accompanying drawings.

DETAILED DESCRIPTION OF THE PREFERRED EMBODIMENT

The following description is intended to convey a thorough understanding of the present invention by providing a number of specific embodiments and details involving use of a material for increasing the stiffness of an intervertebral disc. It is understood, however, that the present invention is not limited to these specific embodiments and details, which are exemplary only. It is further understood that one possessing ordinary-skill in the art, in light of known systems and methods, would appreciate the use of the invention for its intended purposes and benefits in any number of alternative embodiments, depending upon the specific design and other needs.

Description of Relevant Anatomy

Figure 1:
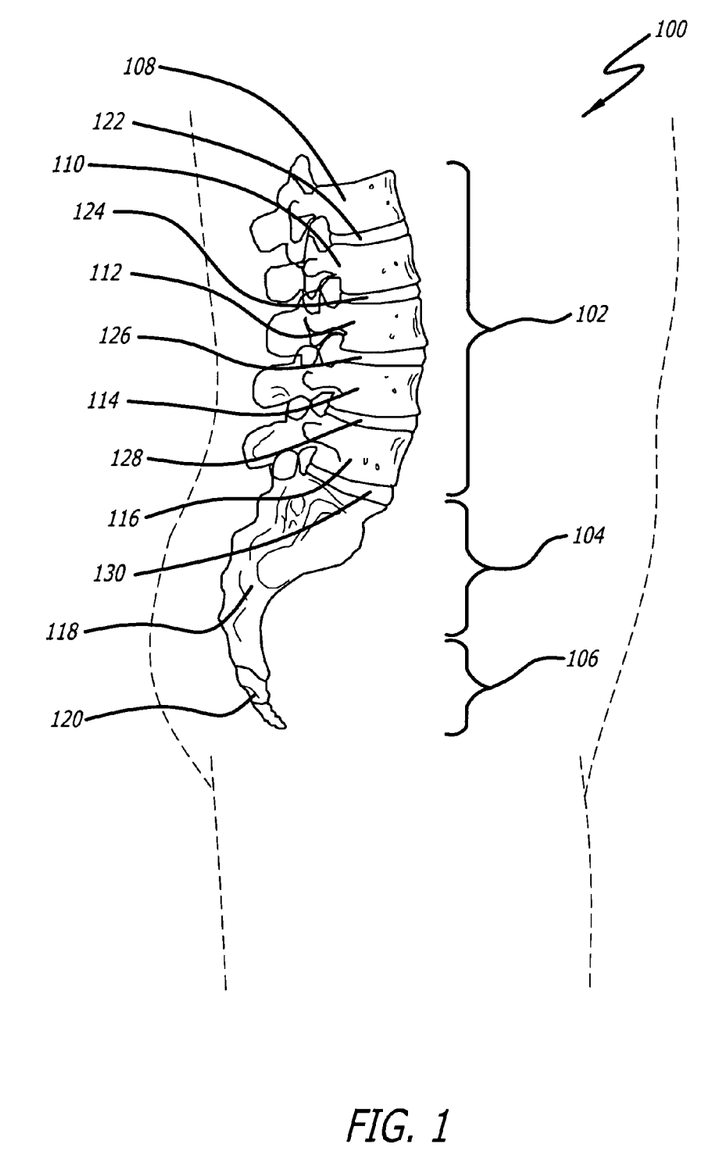
FIG. 1 is a lateral view of a portion of a vertebral column.

As shown in FIG. 1, a portion of a vertebral column, designated 100, is shown. As depicted, vertebral column 100 includes a lumbar region 102, a sacral region 104, and a coccygeal region 106. As is known in the art, vertebral column 100 also includes a cervical region and a thoracic region. For clarity and ease of discussion, the cervical region and the thoracic region are not illustrated.

Lumbar region 102 includes a first lumbar vertebra 108, a second lumbar vertebra 110, a third lumbar vertebra 112, a fourth lumbar vertebra 114, and a fifth lumbar vertebra 116. Sacral region 104 includes a sacrum 118. Further, coccygeal region 106 includes a coccyx 120.

As depicted in FIG. 1, a first intervertebral lumbar disc 122 is disposed between first lumbar vertebra 108 and second lumbar vertebra 110. A second intervertebral lumbar disc 124 is disposed between second lumbar vertebra 110 and third lumbar vertebra 112. A third intervertebral lumbar disc 126 is disposed between third lumbar vertebra 112 and fourth lumbar vertebra 114. Further, a fourth intervertebral lumbar disc 128 is disposed between fourth lumbar vertebra 114 and fifth lumbar vertebra 116. Additionally, a fifth intervertebral lumbar disc 130 is disposed between fifth lumbar vertebra 116 and sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
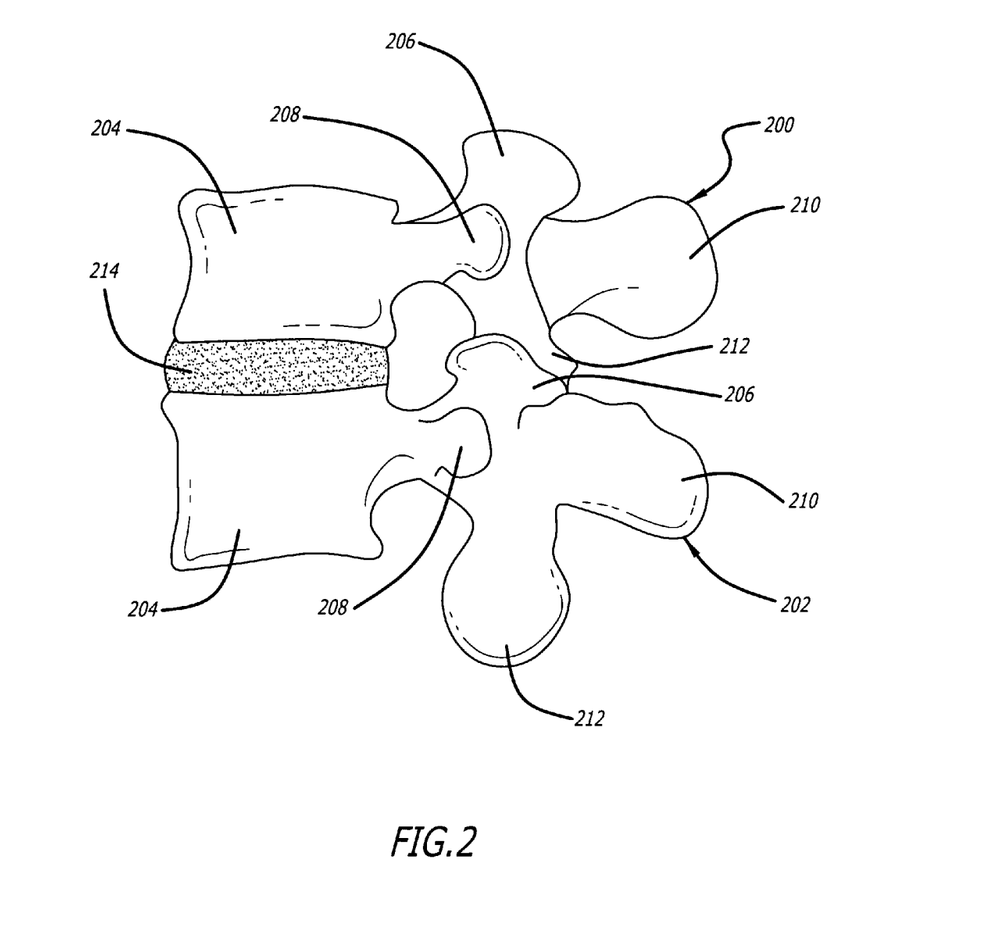
FIG. 2 is a lateral view of a pair of adjacent vertebrae.

FIG. 2 depicts a detailed lateral view of two adjacent vertebrae, e.g., two of lumbar vertebra 108, 110, 112, 114, 116 shown in FIG. 1. FIG. 2 illustrates a superior vertebra 200 and an inferior vertebra 202. As shown, each vertebra 200, 202 include a vertebral body 204, a superior articular process 206, a transverse process 208, a spinous process 210 and an inferior articular process 212. FIG. 2 further depicts an intervertebral disc 214 between superior vertebra 200 and inferior vertebra 202. As described in greater detail below, a material according to one or more of the embodiments described herein can be injected into intervertebral disc 214 for increasing the stiffness of the disc to treat a degenerative or otherwise deleterious condition.

Figure 3:
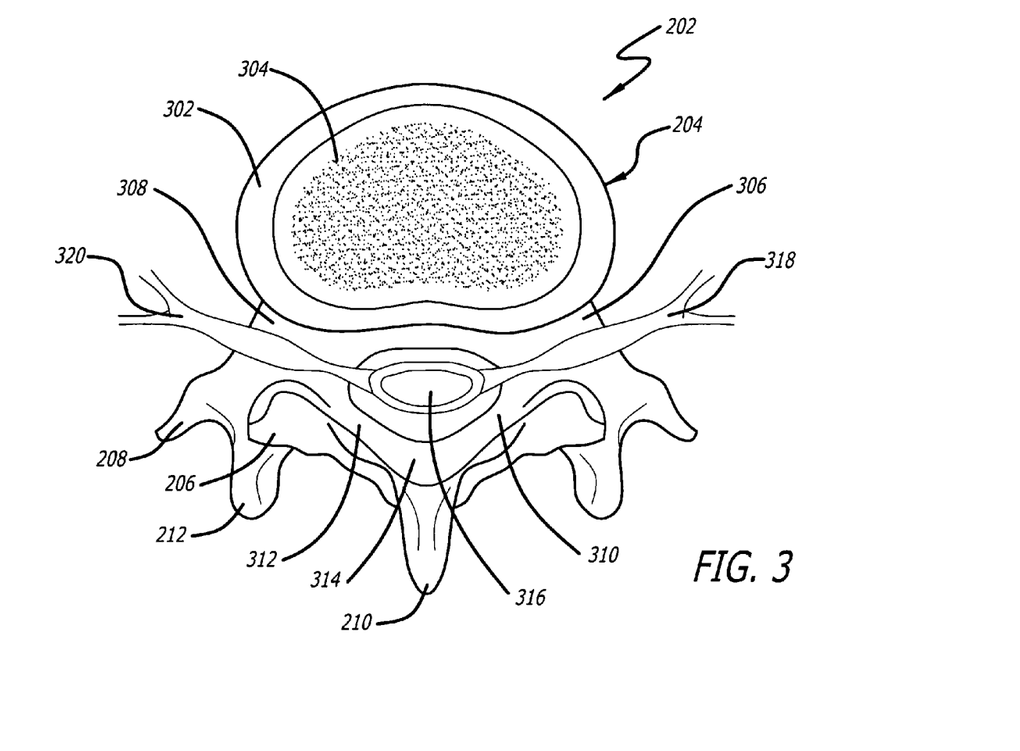
FIG. 3 is a top plan view of a vertebra.

As shown in FIG. 3, a vertebra, e.g., inferior vertebra 202 (FIG. 2), is illustrated. As shown, vertebral body 204 of inferior vertebra 202 includes a cortical rim 302 composed of cortical bone. Also, vertebral body 204 includes cancellous bone 304 within cortical rim 302. Cortical rim 302 is often referred to as the apophyseal rim or apophyseal ring. Further, cancellous bone 304 is softer than the cortical bone of cortical rim 302.

As illustrated in FIG. 3, inferior vertebra 202 further includes a first pedicle 306, a second pedicle 308, a first lamina 310, and a second lamina 312. Further, a vertebral foramen 314 is established within inferior vertebra 202. A spinal cord 316 passes through vertebral foramen 314. Moreover, a first nerve root 318 and a second nerve root 320 extend from spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
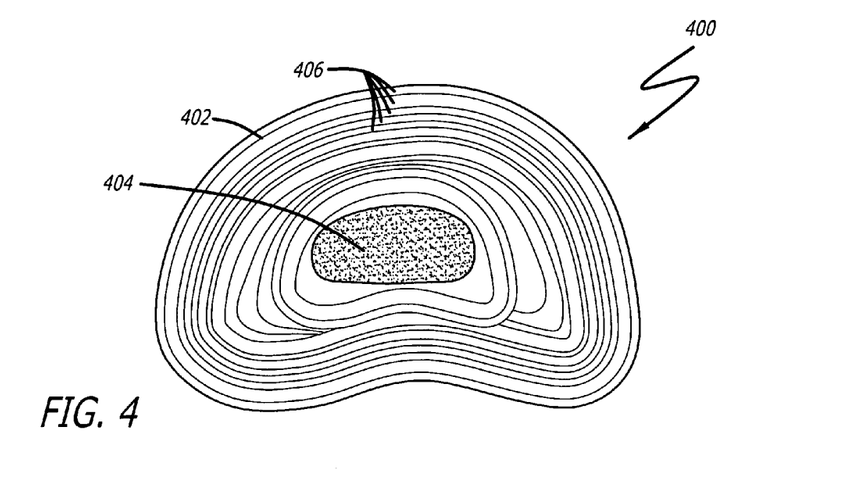
FIG. 4 is a cross-section view of an intervertebral disc.

As shown in FIG. 4, an intervertebral disc is shown and is generally designated 400. Intervertebral disc 400 is made up of two components: annulus fibrosis 402 and nucleus pulposus 404. Annulus fibrosis 402 is the outer portion of intervertebral disc 400, and annulus fibrosis 402 includes a plurality of lamellae 406. Lamellae 406 are layers of collagen and proteins. Each lamella 406 includes fibers that slant at 30-degree angles, and the fibers of each lamella 406 run in a direction opposite the adjacent layers. Accordingly, annulus fibrosis 402 is a structure that is exceptionally strong, yet extremely flexible.

Nucleus pulposus 404 is the inner gel material that is surrounded by annulus fibrosis 402. It makes up about forty percent (40%) of intervertebral disc 400 by weight. Moreover, nucleus pulposus 404 can be considered a ball-like gel that is contained within lamellae 406. Nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of annulus fibrosis 402 may allow nucleus pulposus 404 to be squeezed through the annulus fibers either partially, causing the disc to bulge, or completely, allowing the disc material to escape intervertebral disc 400. The bulging disc or nucleus material may compress the nerves or spinal cord, causing pain. Accordingly, the nucleus pulposus 404 can be removed and replaced with an artificial nucleus. Many of the related art methods are directed to inserting of injecting an intervertebral disc implant into an implantation space formed in the disc after removal of at least a portion thereof.

Description of a Method for Increasing the Stiffness of an Intervertebral Disc

Figure 5:
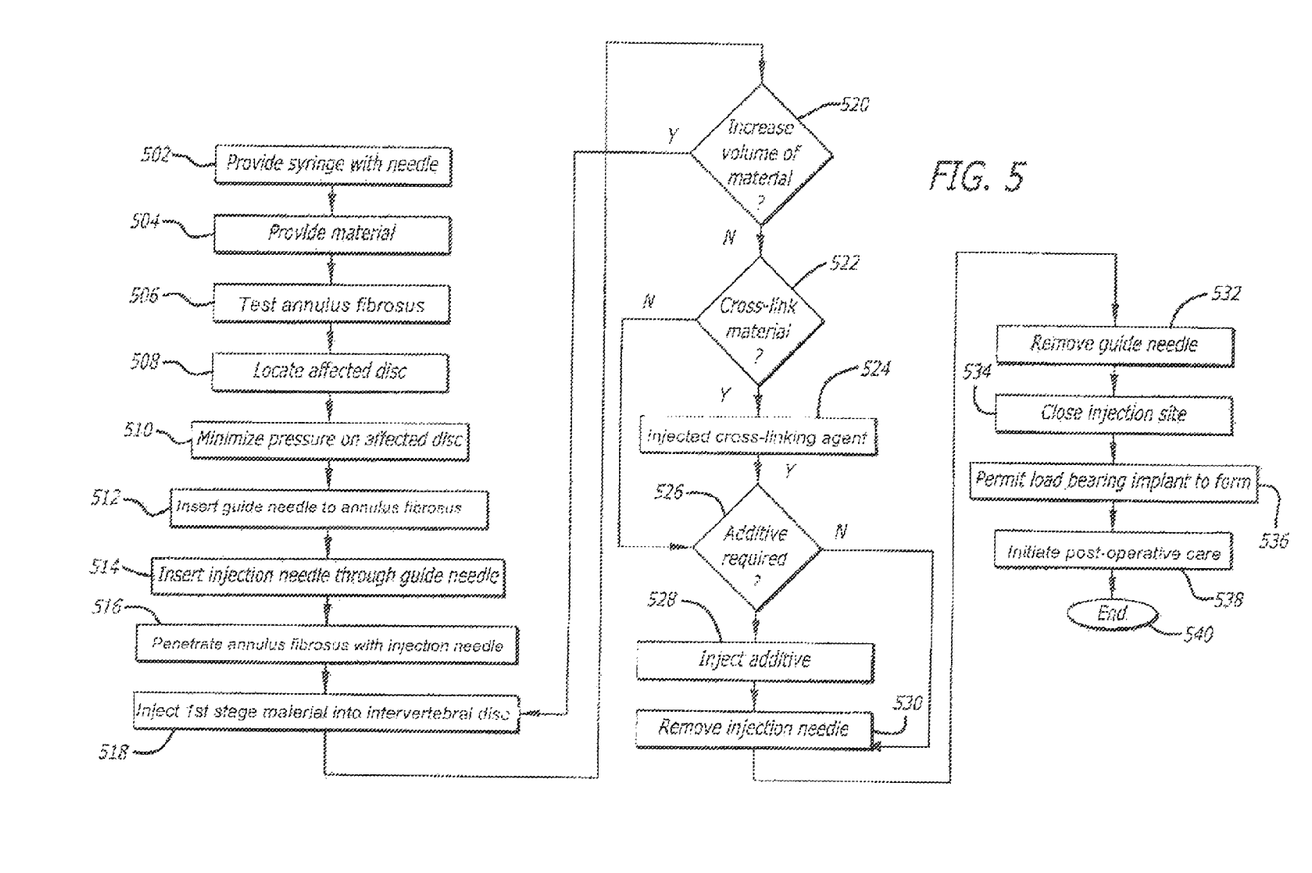
FIG. 5 is a flow chart of a method for increasing the stiffness of an intervertebral disc.

As shown in FIG. 5, a first method of treating an intervertebral disc is illustrated and commences at block 502. At block 502, a syringe with a needle having a distal end approximately in the range of 16 to 25 gauge is provided. In another embodiment, the method may include providing a syringe having a needle having a distal end approximately in a range of 18 to 23 gauge, or more preferably in a range of 19 to 22 gauge.

At block 504, a material having a first stage with a first viscosity adapted to flow through the needle is provided. The material has a second stage with a second viscosity greater than the first viscosity. The second stage material has a stiffness in a range of 1.0-5.0 MPa. The provided material is preferably a polymer and more preferably a hydrogel. The permitting of the first stage material to become the second stage material may include curing the material, which may be a polymer or a hydrogel. The provided material in one embodiment has a second stage material stiffness in a range of 2.0-5.0 MPa, and in another embodiment has a second stage material stiffness in a range of 3.0-5.0 MPa. The provided material in one preferred embodiment includes a water absorption capability in a range of 10-90 percent, and more preferably in a range of 20-80 percent, and yet more preferably in a range of 20-55 percent, 20-40 percent, or 35-55 percent.

At block 506, the annulus fibrosus of the disc is tested, for example, by injecting a fluid into it, to ensure that the annulus fibrosus has sufficient continuity so as to retain the first flowable stage material when subsequently injected into the disc. The testing of the annulus fibrosus may include injecting a fluid in the form of, for example, a dye into the disc to check for fissures, and more preferably injecting a radiolucent contrast solution. This step of a preferred method of the present invention is substantially different from the prior art in that the prior art methods are directed towards patients that typically have a herniated or ruptured disc; thus the patients have significant disc figures. Moreover, the prior art methods do substantial additional damage to the natural disc by typically removing a portion of the entire intervertebral disc.

The testing of the annulus fibrosus to ensure that the annulus will retain the first flowable stage material permits a substantial degree of flexibility in providing a flowable material that might otherwise flow freely from the disc before it forms the second stage load bearing implant. Further, the difficulties of the prior art in attempting to provide a seal to contain the flowable material after removal of a portion or the entire intervertebral disc is avoided. Moreover, in a preferred embodiment the patient may have the disc stiffened via the insertion of a load bearing implant without removal of any portion of the disc itself.

Figure 6:
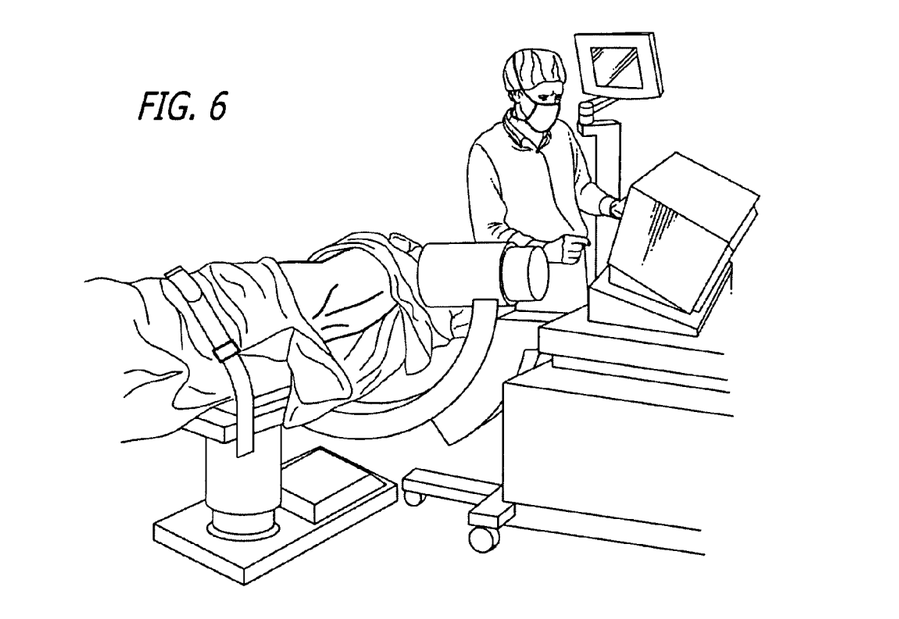
FIG. 6 is a perspective view of an operation room with equipment for patient positioning to aid alignment correction of the spine.

At block 508, the affected intervertebral disc can be located. At block 510, the pressure on the intervertebral disc can be reduced. The pressure on the intervertebral disc can be reduced by placing the patient in a position that reduces loading in the area near the vertebra immediately surrounding the intervertebral disc. By way of example, FIG. 6 illustrates one preferred technique for positioning the patient to aid alignment correction. In another example, the patient can be placed in a prone position on a flexible, or hinged, surgical table, and the patient's spine can be slightly bent by flexing or bending the flexible surgical table around one or more hinges. Further, the patient can be placed in traction in order to reduce pressure on the intervertebral disc. In a particular embodiment, reducing pressure on the intervertebral disc can maximize the amount of material injected therein.

Figure 7:
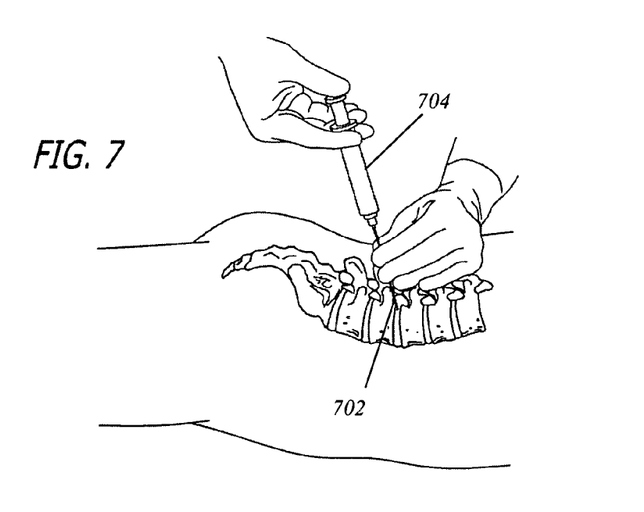
FIG. 7 is a side view with cross sectional view of the spine illustrating a percutaneous injection into the spine.

Moving to block 512, a guide needle can be inserted to the annulus fibrosus of the affected intervertebral disc. In a particular embodiment, the guide needle can be inserted such that the tip of the guide needle is immediately adjacent to the annulus fibrosus, but does not pierce the annulus fibrosus, as illustrated in FIG. 7. At block 514, an injection needle can be inserted through the guide needle. Further, at block 516, the annulus fibrosus can be penetrated with the distal end (tip) of the injection needle. In a particular embodiment, the injection needle can be inserted into the annulus fibrosus such that the tip of the injection needle is approximately near the center of the annulus fibrosus. The location of the tip of the guide needle or the location of tip of the injection needle can be verified using imaging technology, e.g., fluoroscopy, magnetic resonance imaging, computed tomography, or any other similar technology well known in the art.

Proceeding to block 518, first stage material can be injected through the needle and into the intervertebral disc. In one preferred embodiment, the material can be the polymer or hydrogel described herein. Also, in a particular embodiment, the inserting of the distal end of the needle may include inserting the distal end of the needle through the annulus fibrosus only or alternatively through the annulus fibrosus and into the nucleus pulposus of the disc.

Continuing to decision 520, it can be determined whether to increase the volume of material within the nucleus pulposus. This determination can be facilitated using a radio contrast agent injected with the material and imaging technology, e.g., fluoroscopy, magnetic resonance imaging, computed tomography or some other imaging technology well know in the art. At decision 520, if it is determined to increase the volume of material, the method can return to block 518 and more material can be injected into the intervertebral disc. Thereafter, the method can continue as described herein. Conversely, if it is determined not to increase the volume of material, the method can proceed to decision 522 and it can be determined whether to cross-link the material. If so, the method proceeds to block 524 and a cross-linking agent can be injected into the intervertebral disc. In a particular embodiment, the cross-linking agent can be glutaraldehyde, genipin, or a combination thereof. Further, the cross-linking agent can be another protein cross-linking agent. Cross-linking the material can result in a more robust material within the intervertebral disc. From block 524, the method can proceed to decision 526.

Returning to decision 522, if it is determined not to cross-link the collagen material, the method can also proceed to decision 526. At decision 526, it can be determined whether to inject an additive. If it is determined to inject an additive, the method can proceed to block 528 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the intervertebral disc. From block 528, the method can proceed to block 530.

Returning to decision 526, if it is determined not to inject an additive, the method can also proceed to block 530. At block 530, the injection needle can be removed from the patient. Preferably, the puncture left in the disc from the removal of the injection needle is sufficiently small enough that none of the material seeps from the disc, or alternatively, an insignificant amount of the material seeps from the disc, or in a further alternative, the puncture is sufficiently small enough that none the second stage material seeps from the disc. Further, at block 532, the guide needle can be removed from the patient. Moving to block 534, the injection site can be closed. In a particular embodiment, the injection site can simply be allowed to close due to the elasticity of the patient's skin. Alternatively, the injection site can be sutured, if necessary.

At block 536, the first stage material is permitted to become the second stage material. The permitting of the first stage material to become the second stage material includes curing the material. The permitting of the first stage material to become the second stage material forms a load bearing implant in the disc. This load bearing implant may improve the alignment of the vertebral bodies of the spine adjacent the disc. The method may include increasing the disc height with the load bearing implant.

While the permitting of the first stage material to become the second stage material to form a load bearing implant has been described in a preferred embodiment above as occurring after the removal of the injection needle and guide and the closing of the injection site, in another embodiment the material is permitted to form a load bearing implant before the injection needle is remove. This embodiment provides the potential advantage, depending upon the material characteristics, that by keeping the needle at least in part in the disc until the second stage material at least partially forms that first stage material can not potentially flow out through the puncture in the disc left by the removal of the needle. Alternatively, depending upon the flow characteristics, time to transition from a first stage to a second stage, and other aspects of the particular material being used for a particular procedure, the needle may be removed at some point during the transition from first stage material to second stage material.

Proceeding to block 538, post-operative care can be initiated. Then, the method can end at state 540.

The method in one embodiment includes not removing any of the disc before injecting the first stage material through the needle and into the disc. In particular, the method may include not removing any of the annulus fibrosus before injecting the first stage material through the needle and into the disc, or additional or alternatively not removing any of the nucleus pulposus before injecting the first stage material through the needle and into the disc.

A preferred embodiment of the present invention has been described above at block 506 as testing the annulus fibrosus of the disc to ensure that the annulus fibrosus has sufficient continuity so as to retain the first flowable stage material when subsequently injected into the disc. In addition to the testing or as an alternative to the testing, in an alternative embodiment, one may inject a non-toxic biocompatible coating or otherwise protective material into the disc prior to injecting the first stage material. The protective material preferably has the characteristics to coat or otherwise create a barrier within the disc that assists in retaining the first flowable stage material within the disc when subsequently injected into the disc. The protective material may be remain intact for a period of time or alternatively may be bioresorbable.

FIG. 7 illustrates a surgeon makes a percutaneous injection into the spine. A needle 702 is inserted into the spine. Needle 702 can extend from a syringe 704 that can be filled with a material, e.g., a polymer or a hydrogel described herein. The material can be injected into the intervertebral disc in order to increase the stiffness of the intervertebral disc by augmenting or bulking up the intervertebral disc and minimizing shrinkage of the intervertebral disc due to degeneration or trauma.

Figure 8:
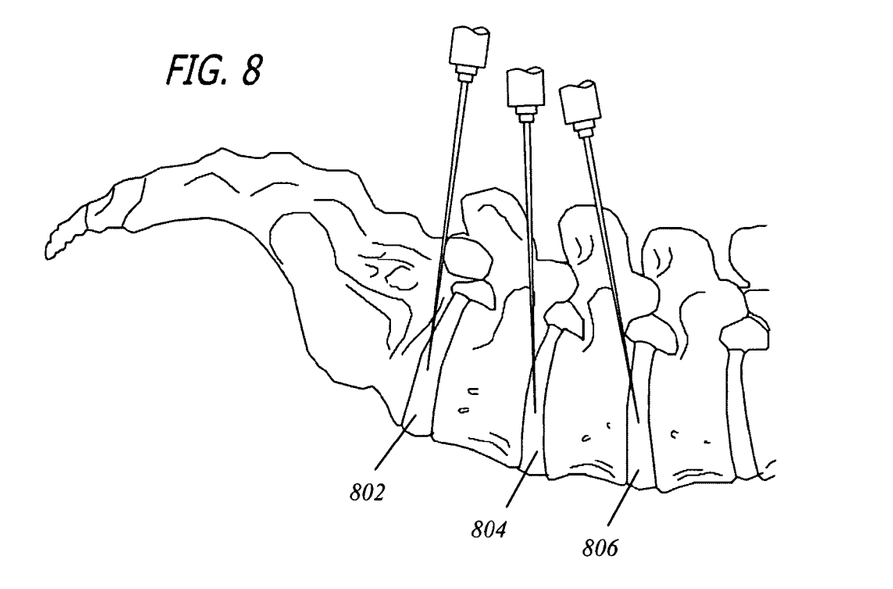
FIG. 8 is a cross-section view of a multiple level segment of a spine with multiple intervertebral discs being injected with material.

FIG. 8 is a cross-section view of a multiple level segment of a spine with multiple intervertebral discs 802, 804, and 806 being injected with material. Many more patients could be helped over a larger portion of their spine with a nonsurgical or minimally invasive treatment method as described herein. Furthermore, the described method and material may be used in conjunction with surgical interventions to improve patient outcomes. While a preferred embodiment of the present method is described in association with a nonsurgical or minimally invasive treatment method, it is contemplated within the scope of the present method that it could be used in certain circumstances with an open procedure, such as during a laminectomy procedure to remove bone spurs, or even during a mini-open procedure.

Figure 9:
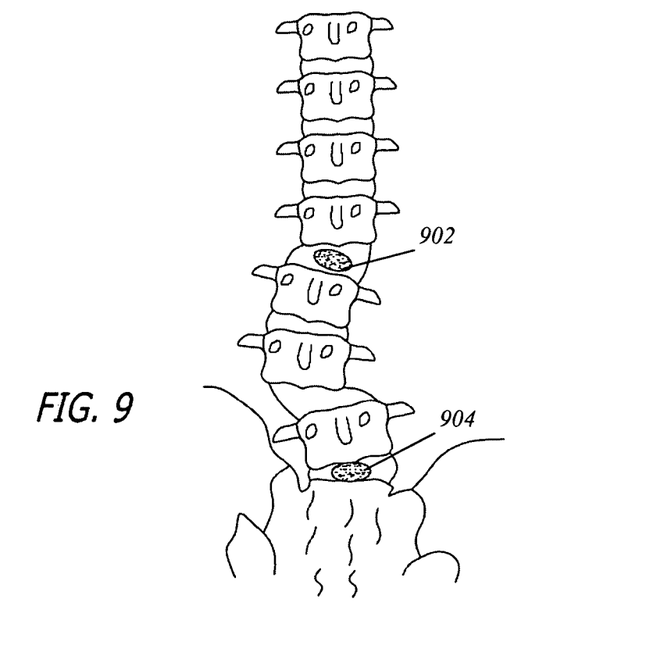
FIG. 9 is a posterior view of a lumbar spine illustrating an example of a potential treatment regime.

FIG. 9 is a posterior view of a lumbar spine illustrating an example of a potential treatment regime. The method described herein may provided one or more implants 902, 904 into the discs of a patient with one or more of the following: a decrease in risk of fracture; improvement in foraminal stenosis, decrease in pain from instability; maintain motion; re-establish lordosis; allow for future surgery, if needed; and may be used in conjunction with arthoplasy devises or any extradiscal stabilization.

Figure 10:
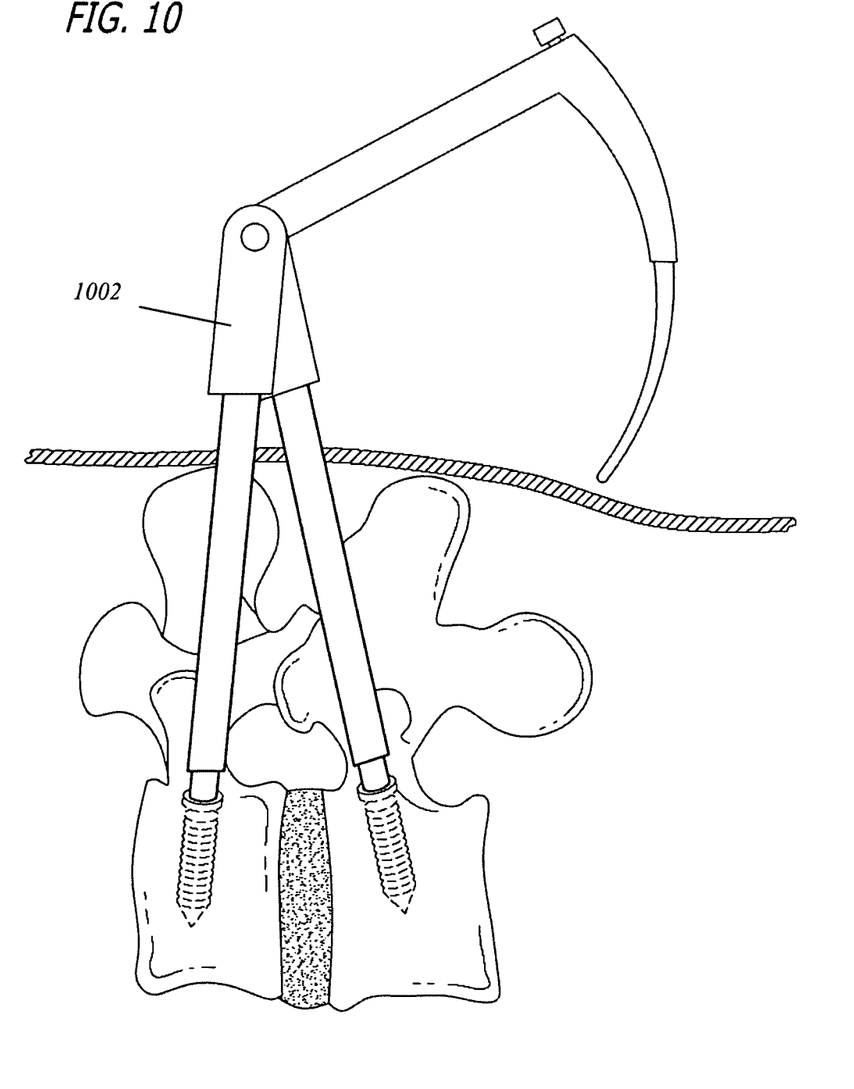
FIG. 10 is a side view of a portion of a patient's spine shown in cutaway illustrating the use of extradiscal instrumentation.

FIG. 10 is a side view of a portion of a patient's spine shown in cutaway illustrating the use of extradiscal instrumentation 1002. Depending on the patient and severity of the condition, the injectable material may be a stand alone treatment, or be used in conjunction with other currently available treatment regimes, such as the CD Horizon Sextant from Warsaw Orthopedic, Inc depicted in use in FIG. 10. One example of the CD Horizon Sextant surgical technique is described in U.S. Pat. No. 7,008,422, incorporated herein by reference in its entirety. The present method also may be used in conjunction with other types of currently available treatments such as but not limited to rigid implant procedures, semi-rigid implant procedures, and motion preserving implant procedures, and in association with their respective instruments. Additionally, the present method may be used in conjunction with external fixation devices including by way of example a peek rod.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for increasing the stiffness of an intervertebral disc between adjacent vertebral bodies of a spine of a patient using a syringe having a needle, and using a material having a first stage with a first viscosity adapted to flow through the needle, the material having a second stage with a second viscosity greater than the first viscosity, the intervertebral disc having an outer region being an annulus fibrosus and a central region being a nucleus pulposus, the method comprising:

injecting a testing liquid into the annulus fibrosus of the disc to determine whether the annulus fibrosus has sufficient continuity to be able to retain the material in the first stage when the material in the first stage is subsequently injected into the disc;

after injecting the testing liquid, inserting a distal end of the needle into the annulus fibrosus, the distal end of the needle being approximately in the range of 16 to 25 gauge;

injecting the material in the first stage through the needle and into the disc without first removing any of the nucleus pulposus, the material in the first stage having the first viscosity, and flowing through the needle and into the disc;

removing the needle from the disc and from the patient while the material is in the disc in the first stage and leaving a puncture in the annulus fibrosus from the removal of the needle from the disc, the puncture being sufficiently small enough to prevent the material in the first stage from seeping from the disc; and permitting the material, after removing the needle from the disc and from the patient, in the first stage to become the material in the second stage so as to form a load bearing implant in the disc to increase the stiffness of at least a portion of the disc, the material in the second stage having a stiffness in a range of 1.0-5.0 MPa.

2. The method of claim 1, wherein the inserting a distal end of the needle includes inserting the needle having the distal end approximately in a range of 18 to 23 gauge.

3. The method of claim 1, wherein the inserting a distal end of the needle includes inserting the needle having the distal end approximately in a range of 19 to 22 gauge.

4. The method of claim 1, wherein the material includes a polymer.

5. The method of claim 4, wherein the permitting the material in the first stage to become the material in the second stage includes curing the polymer.

6. The method of claim 1, wherein the material includes a hydrogel.

7. The method of claim 6, wherein the permitting the material in the first stage to become the material in the second stage includes curing the hydrogel.

8. The method of claim 1, wherein the material in the second stage has a stiffness in a range of 2.0-5.0 MPa.

9. The method of claim 1, wherein the material in the second stage has a stiffness in a range of 3.0-5.0 MPa.

10. The method of claim 1, wherein the material has a water absorption capability in a range of 10-90 percentage.

11. The method of claim 10, wherein the water absorption capability of the material is in a range of 20-80 percentage.

12. The method of claim 10, wherein the water absorption capability of the material is in a range of 20-55 percentage.

13. The method of claim 10, wherein the water absorption capability of the material is in a range of 20-40 percentage.

14. The method of claim 10, wherein the water absorption capability of the material is in a range of 35-55 percentage.

15. The method of claim 1, wherein the injecting the testing liquid into the annulus fibrosus includes injecting a dye into the disc to check for fissures.

16. The method of claim 15, wherein the injecting the dye includes injecting a radiolucent contrast solution.

17. The method of claim 1, wherein the inserting a distal end of the needle includes inserting the distal end of the needle through the annulus fibrosus and into the nucleus pulposus of the disc.

18. The method of claim 1, wherein the injecting the material in the first stage through the needle and into the disc includes injecting a polymer into the nucleus pulposus of the disc.

19. The method of claim 1, wherein the injecting the material in the first stage through the needle and into the disc includes injecting a hydrogel into the nucleus pulposus of the disc.

20. The method of claim 1, wherein the permitting the material in the first stage to become the material in the second stage includes curing the material.

21. The method of claim 1, wherein the permitting the material in the first stage to become the material in the second stage so as to form the load bearing implant in the disc improves the alignment of the vertebral bodies of the spine adjacent the disc.

22. The method of claim 1, wherein the permitting the material in the first stage to become the material in the second stage so as to form the load bearing implant in the disc increases lordosis of the vertebral bodies of the spine adjacent the disc.

23. The method of claim 1, wherein the permitting the material in the first stage to become the material in the second stage so as to form the load bearing implant in the disc stiffens motion between the vertebral bodies of the spine adjacent the disc.

24. The method of claim 1, wherein the permitting the material in the first stage to become the material in the second stage so as to form the load bearing implant in the disc indirectly decompresses nerve compression in the neuroforamina of the spine proximate the disc.

25. The method of claim 1, further comprising increasing the disc height with the load bearing implant.

26. The method of claim 1, further comprising inserting a guide needle to a position proximate but not piercing the annulus fibrosus to guide the injection needle into the annulus fibrosus.

27. The method of claim 1, further comprising not removing any of the disc before injecting the material in the first stage through the needle and into the disc.

28. The method of claim 1, further comprising not removing any of the annulus fibrosus before injecting the material in the first stage through the needle and into the disc.

29. The method of claim 1, further comprising positioning the patient to reduce loading in the area near the vertebra immediately surrounding the disc and to reduce pressure on the disc.

30. The method of claim 1, further comprising stabilizing the spine with an external fixation device.

31. The method of claim 30, wherein stabilizing the spine with the external fixation device includes stabilizing with a peek rod.

32. The method of claim 1, wherein inserting the distal end of the needle includes percutaneously inserting the needle through the patient's skin.

33. The method of claim 32, further comprising removing the needle from the injection site and permitting the injection site to close due to the elasticity of the patient's skin.

34. The method of claim 32, further comprising removing the needle from the injection site and permitting the injection site to dose.

35. A method for increasing the stiffness of an intervertebral disc between adjacent vertebral bodies of a spine of a patient using a syringe having a needle, and using a material having a first stage with a first viscosity adapted to flow through the needle and into the intervertebral disc, the material having a second stage with a second viscosity greater than the first viscosity, the intervertebral disc having an outer region being an annulus fibrosus and a central region being a nucleus pulposus, the method comprising:

injecting a testing fluid into the annulus fibrosus of the disc to determine whether the annulus fibrosus has sufficient continuity to be able to retain the material in the first stage when the material in the first stage is subsequently injected into the disc;

inserting a distal end of the needle into the disc;

subsequently injecting the material in the first stage through the needle and into the disc without first removing any of the nucleus pulposus, the distal end of the needle being approximately in the range of 16 to 25 gauge;

removing the needle from the disc and from the patient while the material is in the disc in the first stage and leaving a puncture sufficiently small to prevent leakage of the material in the first stage from the disc after removal of the needle; and permitting, after removing the needle from the disc and from the patient, the material in the first stage to become the material in the second stage so as to form a load bearing implant in the disc to increase the stiffness of at least a portion of the disc, the material in the second stage having a stiffness in a range of 1.0-5.0 MPa.

36. A method for increasing the stiffness of an intervertebral disc between adjacent vertebral bodies of a spine of a patient using a syringe having a needle, and using a material having a first stage with a first viscosity adapted to flow through the needle, the material having a second stage with a second viscosity greater than the first viscosity, the intervertebral disc having an outer region being an annulus fibrosus and a central region being a nucleus pulposus, the method comprising:

injecting a testing liquid into the annulus fibrosus of the disc;

inspecting the annulus fibrosus for the presence of leakage of the testing liquid indicating the existence of any fissures in the annulus fibrosus;

after injecting the testing liquid and inspecting the annulus fibrosus, inserting a distal end of the needle into the annulus fibrosus, the distal end of the needle being approximately in the range of 16 to 25 gauge;

injecting the material in the first stage through the needle and into the disc without first removing any of the nucleus pulposus, the material in the first stage having the first viscosity, and flowing through the needle and into the disc;

removing the needle from the disc and from the patient while the material is in the disc in the first stage and leaving a puncture in the annulus fibrosus from the removal of the needle from the disc and from the patient, the puncture being sufficiently small enough to prevent the material from seeping from the disc; and permitting the material, after removing the needle from the disc and from the patient, in the first stage to become the material in the second stage so as to form a load bearing implant in the disc to increase the stiffness of at least a portion of the disc, the material in the second stage having a stiffness in a range of 1.0-5.0 and MPa.

* * * * *

UNITED STATES PATENT AND TRADEMARK OFFICE
CERTIFICATE OF CORRECTION

PATENT NO. : 8,864,801 B2  
APPLICATION NO. : 11/796757  
DATED : October 21, 2014  
INVENTOR(S) : Dennis G. Crandall et al.

Page 1 of 1

It is certified that error appears in the above-identified patent and that said Letters Patent is hereby corrected as shown below:

In the Claims:  
Column 12, Claim 34:  
Line 38: change "dose" to -- close --.

Column 14, Claim 36:  
Line 17: delete "and".

Signed and Sealed this  
Sixth Day of January, 2015

Michelle K. Lee  
*Deputy Director of the United States Patent and Trademark Office*